United States Patent
Sahner

(10) Patent No.: US 6,573,696 B1
(45) Date of Patent: Jun. 3, 2003

(54) EVALUATION METHOD FOR A PARTICLE COUNTER AND DEVICE FOR CARRYING OUT SAID METHOD

(75) Inventor: Paul Sahner, Dillingen (DE)

(73) Assignee: Hydac Filtertechnik GmbH, Sulzbach/Saar (DE)

( * ) Notice: Subject to any disclaimer, the term of this patent is extended or adjusted under 35 U.S.C. 154(b) by 0 days.

(21) Appl. No.: 09/807,286
(22) PCT Filed: Oct. 21, 1998
(86) PCT No.: PCT/EP98/06670
§ 371 (c)(1), (2), (4) Date: Apr. 11, 2001
(87) PCT Pub. No.: WO00/23787
PCT Pub. Date: Apr. 27, 2000

(51) Int. Cl.[7] .......................... G01N 27/00; G06M 1/10; G06F 19/00
(52) U.S. Cl. ................... 324/71.4; 324/76.16; 324/601; 324/606; 702/23; 702/26
(58) Field of Search ............................... 324/71.4, 436, 324/601, 606, 607, 76.16; 702/21, 26, 23, 85, 29; 377/11

(56) References Cited

U.S. PATENT DOCUMENTS 4,165,484 A * 8/1979 Haynes et al. ............. 324/71.4
4,491,926 A * 1/1985 Okada et al. ............... 324/71.4
5,365,559 A * 11/1994 Hsueh et al. ............... 324/71.4
6,259,242 B1 * 7/2001 Graham et al. ............. 324/439

FOREIGN PATENT DOCUMENTS

DE   12 94 051 B   4/1969
GB   2 082 764 A   3/1982

* cited by examiner

Primary Examiner—N. Le
Assistant Examiner—Anjan K. Deb
(74) Attorney, Agent, or Firm—Roylance, Abrams, Berdo & Goodman, L.L.P.

(57) ABSTRACT

In an evaluation method for a particle counter, a detector generates a signal in response to the presence of particles in a measuring area in which a liquid flow is conveyed. The sensor signal is treated by a signal processing device and is converted into a display value, taking into account at least one calibration factor. The sensor signal is treated in such a way that the individual residence times of the particles in the measuring zone are determined within a given lapse of time and a summated signal is formed by summating the residence times. The signal is used to represent the display value, taking into account the at least one calibration factor. A device for carrying out this includes a signal processing unit with a comparator circuit, a clock-pulse generator and a summation device in the form of a pulse counter, for example, in order to form the summated signal.

7 Claims, 3 Drawing Sheets

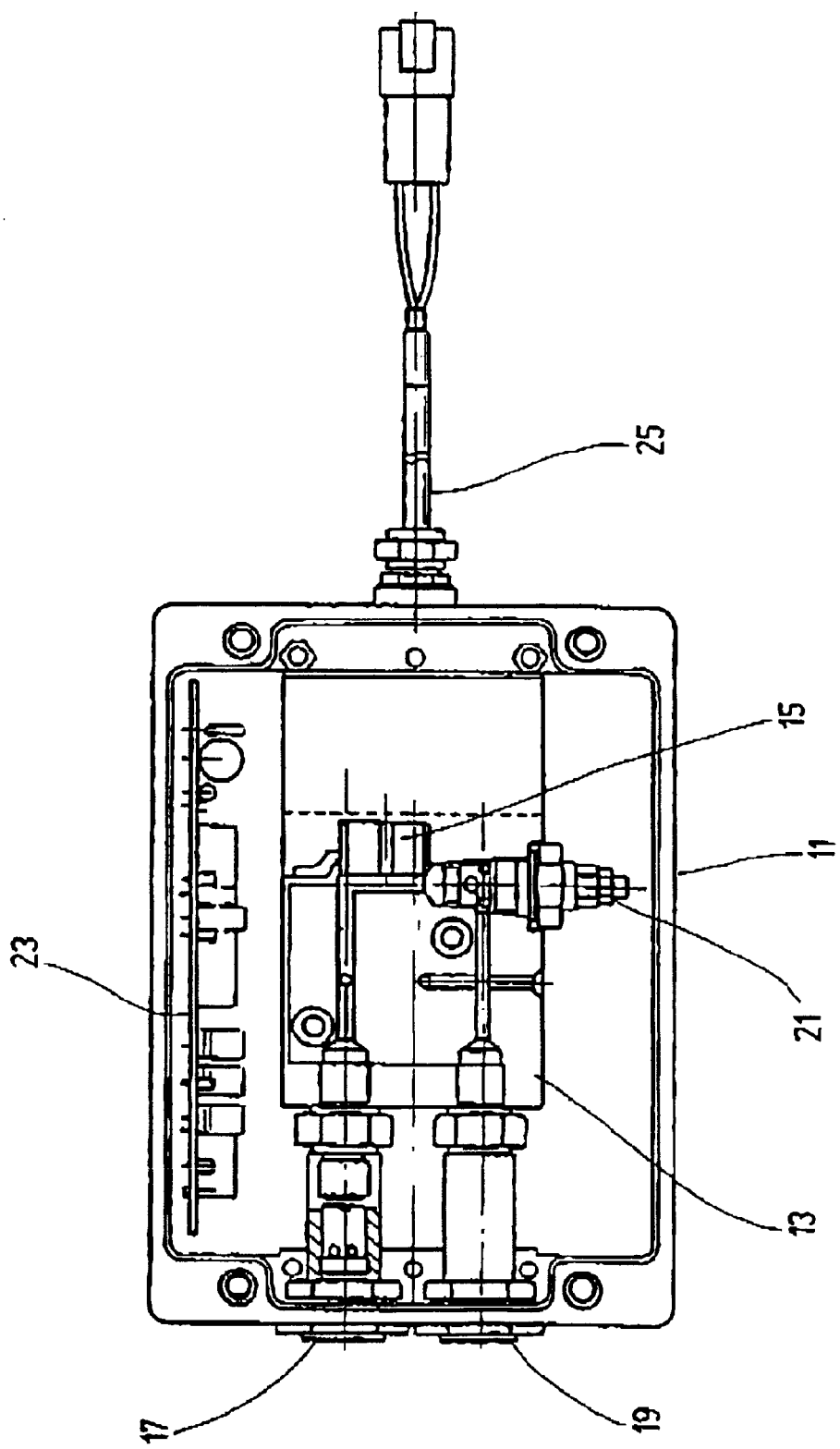

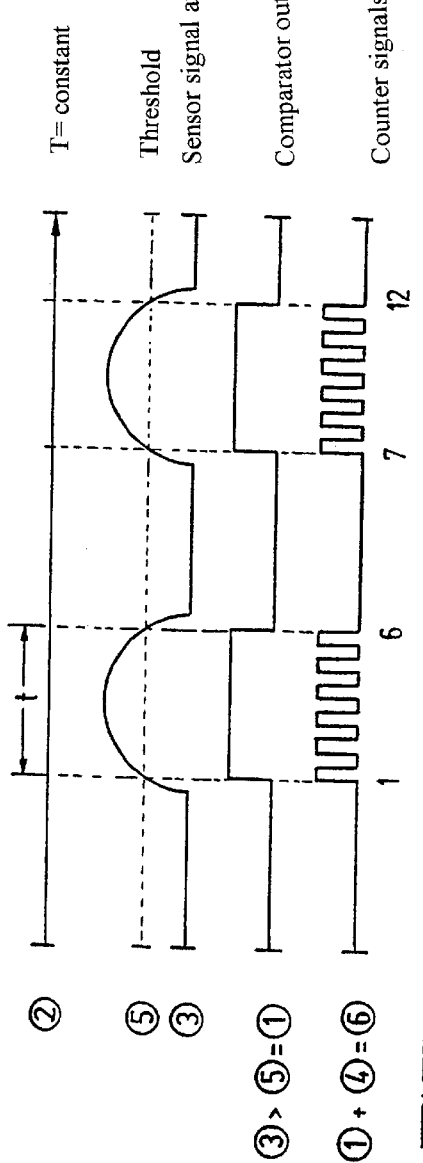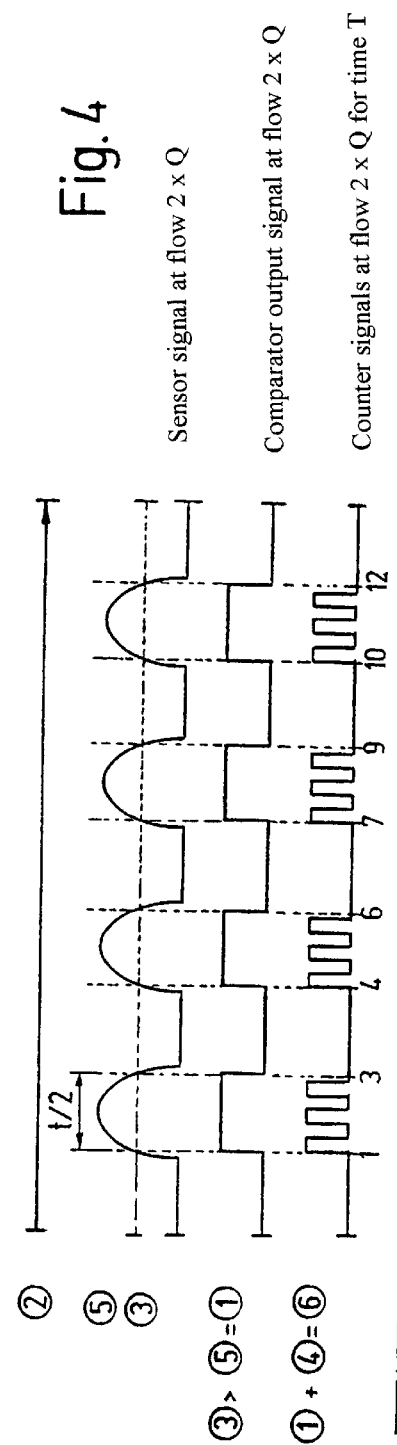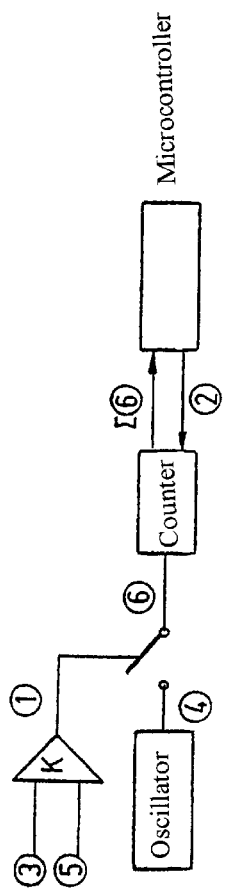

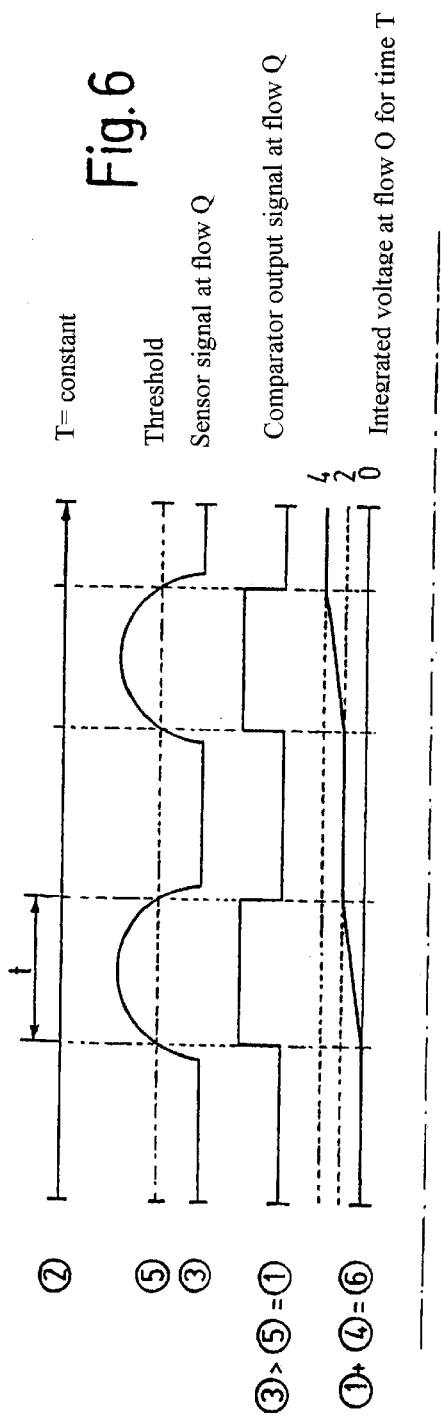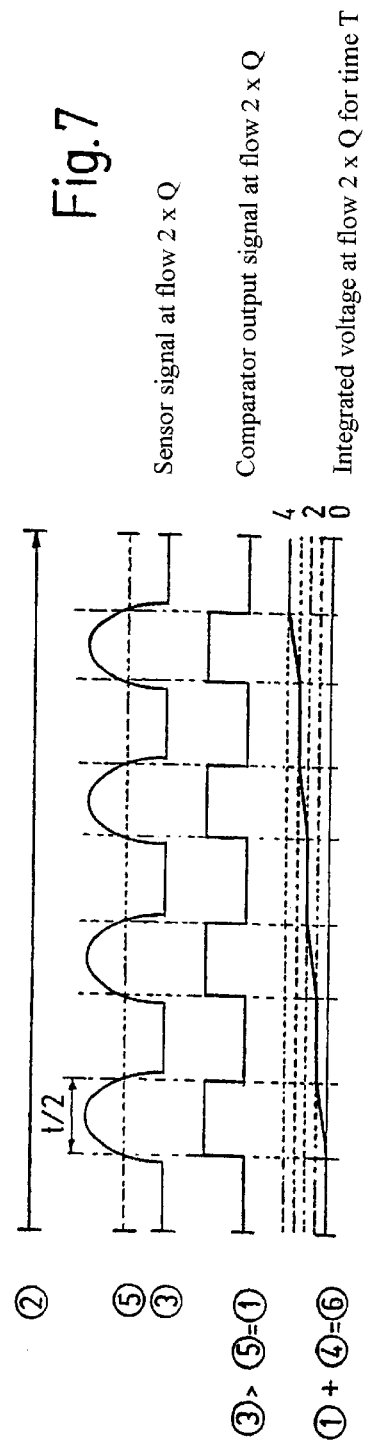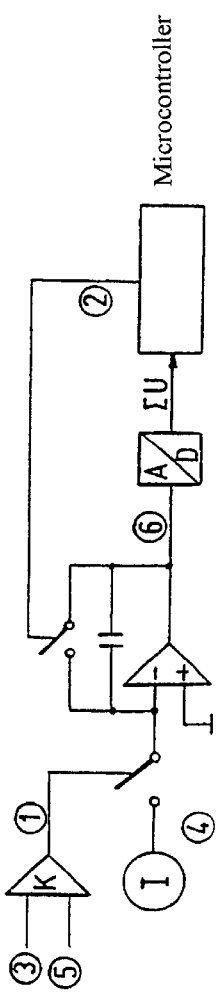

EVALUATION METHOD FOR A PARTICLE COUNTER AND DEVICE FOR CARRYING OUT SAID METHOD

FIELD OF THE INVENTION

The present invention relates to an evaluation method for a particle counter in which a detector signal is produced by means of a detector. The detector reacts to the presence of particles in a measuring zone in which a liquid flow is being conveyed. The detector signal is treated by a signal processing device and, taking into account at least one calibration factor, is converted into a display value indicating the particle density of the liquid flow. The present invention also relates to a device for carrying out the evaluation method.

BACKGROUND OF THE INVENTION

European Patent 0 427 908 discloses a particle counter working by the opacity method and including a light enclosure. The light enclosure receiver produces detector signals showing the presence of opaque particles in the measuring zone. An evaluation method of this type is used in the evaluation of these detector signals, carried out by the method disclosed in DE 41 10 231 A1. The degree of contamination of the liquid flow flowing through the measuring zone is to be monitored, preferably with hydraulic petroleum. The densities of charges of solid materials, such as metallic and nonmetallic impurities or contaminants, in the liquid are established. Even the presence of air bubbles or water droplets in the light enclosures likewise lead to the appearances of opacities which appear on the detector signal.

In the conventional evaluation method, particles present in a certain volume to be measured are counted in channels of different magnitudes, associated with particles which are in classes of different magnitudes and in turn are counted as pulses of the detector signal. The volume to be measured in turn is determined by volume flow measurement. The particle count is then corrected by multiplication with the relevant channel magnitudes of corresponding individual calibration factors. These corrected particle numbers are then translated into classes of contamination in order to correspond to the NAS 1638- or ISO 4406-Tables.

DE 1 294 051 B discloses a method and device for the measurement of the volume or weight of a volume of essentially nonuniform bodies being conveyed through a channel of predetermined diameter. In this case, the detector signal is converted by means of a trigger stage into pulses of constant amplitude. These pulses are fed to an integrator, in which occurs a time integration of the discrete individual pulses. Following each pulse, the output signal of the integrator is returned to start. The method supplies an output signal which represents a mean value of the volume or weight of the bodies conveyed in a time lapse to be studied.

GB 2 082 764 A discloses a device for measuring particles in liquids in which the appearance of particles is established as a phenomenon, and the phenomena are summarized by means of a counter. When a predetermined number of phenomena has been exceeded, a switch is activated, which can set off an alarm or react otherwise. For determination of the particle density, additional and independent measurements of the volume flow must be carried out.

SUMMARY OF THE INVENTION

Objects of the present invention are to provide a method of evaluation which, as opposed to the conventional method, is characterized in that the density of the particle charge of the relevant liquid flow can be evaluated at lower cost and with greater precision.

With an evaluation method of this type, these objects are attained according to the present invention by the treatment of the detector signal being carried out in such a manner that the individual residence times of the particles in the measuring zone are determined within a predetermined lapse of time. By summation of the residence times, a summation signal is formed. This summation signal is used, taking into account at least one calibration factor, for the representation of the display value.

Since the display value is no longer determined on the basis of the counted number of particles present in a certain liquid volume, but rather on the basis of a summation of the individual residence times of the particles within the zone of measurement carried out within a certain predetermined lapse of time, the measurement of the volume flow, which is required in the conventional method, as well as other measures which have been required in cooperation with the conventional method, can be deleted. Thus, the method according to the present invention is characterized not only by simplified capacity of execution with decreased outlay of apparatus, but also by a comparably higher precision in the results. Since no knowledge concerning the present volume flow is required, the evaluation is dependent neither on any measurement or limitation of the volume flow being considered nor of its condition otherwise. Regarding a higher level of precision, the circumstance is also to be considered that no error of the volume flow measurement need be taken into consideration for the calculations.

One method for ascertaining the distribution of the particle dimensions of the particles dispersed in liquids is disclosed in DE 32 09 510 C2 and U.S. Pat. No. 4,491,926, by determining the residence times of particles in the measuring zone. Differing from that disclosure, the method according to the present invention carries out the treatment of the detector signal in such a manner that residence times of the particles in the measuring zone are determined on the basis of the number of counted pulses.

As in the conventional evaluation method, in the present invention the evaluation can be based on the different classes according to particle size, as found in the so-called magnitude-channels. A suitable calibration factor is used for each relevant channel magnitude, for the determination of the display value. Thus, the particle number per liquid volume can be deduced from the summation signal, for example the count per 100 ml, so that in turn the correlation to classes of contaminants relating to this particle number can be undertaken corresponding to the NAS 1638- or ISO 4406-Tables relating thereto.

For evaluation of the pulse height in the detector signal for correlation to the channel magnitudes, the detector signal can be converted by means of a comparator circuit into a comparator output signal representing the residence times while taking into account a predetermined threshold value. The output signal is used for the summation of the residence times and can be analog or digital. With the analog determination, the comparator output signal is integrated within the predetermined lapse of time to a voltage value representing a summation signal. With the digital determination, according to one preferred embodiment, it is carried out so that the summation of the residence times is demonstrated in such a manner that oscillator pulses are counted, which have been released within the predetermined lapse of time according to the measure of the comparator output signal.

According to one other aspect of the present invention, a device for execution of the disclosed evaluation method is provided. The device of the present invention includes a signal processing device with a comparator circuit for generation of a comparator output signal representing the residence times of the particles in the measuring zone, while taking into consideration a predetermined threshold value. A pulse generator produces a pulse signal defining the predetermined lapse of time, as well as with a summation device.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure:

FIG. 1 is a diagrammatically simplified, partially cut out plan view of an arrangement including particle counter and associated evaluation device, with cover removed form the device, according to the present invention;

FIG. 2 is a greatly simplified block diagram of one embodiment of the signal processing device for use with the modular unit of the device of FIG. 1;

FIGS. 3 and 4 are diagrams of the temporal cycle of signal pulses of the signal processing device of FIG. 2;

FIG. 5 is a block diagram corresponding to that of FIG. 2 of a second embodiment of the signal processing device of FIG. 1; and FIGS. 6 and 7 are diagrams corresponding to FIGS. 3 and 4 of the temporal cycle of signal pulses form the signal processing device of FIG. 5.

DETAILED DESCRIPTION OF THE INVENTION

A modular unit, shown in FIG. 1, has an aluminum housing 11 with the cover removed, receiving a detector module 13 with a particle detector 15. The particle detector is a conventional detector as disclosed in European Patent 0 427 908, and produces detector signals according to the opacity principle by means of a light enclosure arrangement. The light enclosure arrangement transmits signals representing the presence of particles in a measuring zone. For the feed and the discharge of the liquid flowing through the measuring zone, housing 11 has a liquid inlet 17 and a liquid outlet 19. Detector module 13 also incorporates a pressure valve 21 to facilitate the shutting off on a pressure-loaded conduit.

A signal processing device 23, serving as evaluation circuit for the detector signals of the particle detector 15, likewise is mounted in housing 11. The power supply or power source for particle detector 15 and for signal processing device 23 is connected through a cable 25. The output signal is also delivered through cable 25. The output signal characterized by a NAS-contamination class and, for example, is published as pulse duration modulated square-wave signal. One example of a digital evaluation method for the production of such an output signal is explained in greater detail relative to FIGS. 2 to 4.

In FIGS. 2–4, (2) symbolizes a time signal defining a predetermined lapse of time, and is fed from the pulse generator of a controller unit; (3) symbolizes the detector signal of particle detector 15; (5) is a threshold value signal; (1) symbolizes a comparator output signal produced by operation of the comparator out of signals (3) and (5); and (6) symbolizes counter or counted signal pulses appearing when oscillator pulses (4) are being released by the comparator output signal (1).

FIG. 3 shows one example in which with a given flow rate Q of the flowing liquid during the predetermined lapse of time T=constant (for example one minute). The detector signal (3) signals the presence of two particles, and with the selected threshold value (5), the output signal (1) of a comparator circuit, indicated in FIG. 2 with K, indicates a residence time denoted by t for each particle.

In the case of the present oscillator frequency (4), its release leads through the comparator output signal over each of the residence times t to six counter pulses for each one. At the end of the lapse of time T, such lead to a summarized counter state of 12 (see FIG. 3).

FIG. 4 shows the ratio with the identical liquid, in other words liquid having the same particle density as in FIG. 2. However, the flow rate of the liquid is 2×Q, in other words double the rate shown in FIG. 3. This doubled flow rate of the liquid having the identical particle density leads to the appearance of a detector signal (3). Dector signal (3) signals four particles collected by the detector. However, the individual residence time is only t/2 as a result of the doubled flow rate. With identical oscillator frequency and with any individual residence time of t/2 in turn three counter pulses (6) appear, which in turn, within the time lapse T including four summarized residence times t/2, lead to the identical counter state 12 with the flow rate 2×Q. The state of the counter following the running out of the time interval T is independent of the flow rate which is the identical rate. By customary calculation with suitable calibration factors therefore from the counter state the particle density or the degree of contamination can be deduced according to NAS or ISO.

FIGS. 5 to 7 show one possible arrangement for analog evaluation, whereby a current source 1 is diagrammatically represented in FIG. 5. In FIGS. 6 and 7, corresponding to FIGS. 3 and 4, the ratios with flow rate Q or flow rate 2×Q are represented in turn. As signaled previously, with the flow rate 2×Q, the comparator output signal (1), with given threshold (5), delivers double the number of residence times as compared with FIG. 6, whereby the individual residence times as compared with t of FIG. 6 are decreased to t/2 in FIG. 7. The voltage integrated by means of an integrator in the circuit of FIG. 5, according to the measure of the comparator output signal (1), rises in the example of FIG. 6 during each of the individual residence times t in terms of two voltage units, so that the integrated voltage with the flow rate Q is referenced according to the lapse of time T as four voltage units.

In the example of FIG. 7 the voltage (6) is modified on the basis of the halved residence time t/2 in turn for one voltage unit only, which following running out of the time lapse T with the doubled flow rate 2×Q likewise leads to the integrated value of four voltage units. The evaluation result is likewise again independent of the flow rate.

While various embodiments have been chosen to illustrate the invention, it will be understood by those skilled in the art that various changes and modifications can be made therein without departing from the scope of the invention as defined in the appended claims.

What is claimed is:

1. A method for evaluating a particle counter, comprising the steps of:
producing a detector signal by a detector reacting to presence of particles in a measuring zone through which a liquid flow is conveyed; and treating the detector signal by a signal processing device and converting the detector signal into a display value, while taking into account at least one calibration factor, such that the display value indicates a particle density in the liquid flow by ascertaining the individual residence times of the particles in the liquid flow in the measuring zone and within a predetermined lapse of time and by performing a summation of the residence times to form a summation signal, while taking into account the at least one calibration factor, for representing the display value.

2. A method according to claim 1 wherein the detector signal is converted by a comparator circuit into a comparator output signal representing the residence time and taking into account a predetermine threshold value; and comparator output signals are summed for the summation of the residence times.

3. A method according to claim 2 wherein oscillation pulses are released within the predetermined lapse of time according to a measure of the comparator output signal and are counted with the summation of the residence times.

4. A method according to claim 2 wherein the summation of the residence times is performed by integration of the comparator output signal; and signal values produced within the predetermine lapse of time are summated with the summation of the residence times.

5. A method according to claim 4 wherein the summated signal values are digitized by an analog-digital converter.

6. A device for evaluating a particle counter, comprising a detector for producing a signal reacting to presence of particles in a measuring zone through which a liquid flow is conveyed;

a signal processing device, including a comparator circuit, for generating a comparator output signal representing residence times of the particles in said measuring zone, taking into account a predetermined threshold value;

a pulse generator for producing a pulse signal defining a predetermined lapse of time; and a summation device for forming a summation of the comparator output signal, taking into account the at least one calibration factor, to represent a display value indicating particle density in the liquid flow.

7. A device according to claim 6 wherein said signal processing device comprises an oscillator which releases oscillator pulses according to measurements of the comparator output signal;

a counter, coupled to said signal processing device, counts the oscillator pulses within the predetermined lapse of time.

* * * * *